United States Patent [19]

Duddu et al.

[11] Patent Number: 6,015,898

[45] Date of Patent: Jan. 18, 2000

[54] PROCESSES AND COMPOSITIONS FOR NITRATION OF N-SUBSTITUTED ISOWURTZITANE COMPOUNDS WITH CONCENTRATED NITRIC ACID AT ELEVATED TEMPERATURES TO FORM HNIW AND RECOVERY OF GAMMA HNIW WITH HIGH YIELDS AND PURITIES

[75] Inventors: Raja G. Duddu, Budd Lake; Paritosh R. Dave, Bridgewater, both of N.J.

[73] Assignee: The United States of America, as represented by the Secretary of the Army, Washington, D.C.

[21] Appl. No.: 09/071,022

[22] Filed: May 1, 1998

[51] Int. Cl.$^7$ .......................... C07D 255/04; C06B 25/34
[52] U.S. Cl. ............................. 540/554; 540/556; 149/92
[58] Field of Search ................................. 540/554, 556; 149/92

[56] References Cited

U.S. PATENT DOCUMENTS 5,693,794  12/1997  Nielsen ................................... 540/554
5,712,511  1/1998  Chan et al. ................................ 264/3.4
5,739,325  4/1998  Wardle et al. ............................ 540/554

FOREIGN PATENT DOCUMENTS 0 753 519    1/1997   European Pat. Off.
06321962    11/1994   Japan.
WO 97/05666  2/1998   WIPO.

OTHER PUBLICATIONS

Chemical Abstracts, vol. 128, No. 14, 1998, No. 167, 452 Kawabe et al Process for Preparation Etc.

*Primary Examiner*—Mukund J. Shah
*Assistant Examiner*—Brenda Coleman
*Attorney, Agent, or Firm*—John F. Moran; Michael C. Sachs; John E. Callaghan

[57] ABSTRACT

Processes and compositions for nitration of N-substituted isowurtzitane compounds with concentrated nitric acid at elevated temperatures to form HNIW and recovery of gamma HNIW with high yields and purities. Polymorphic conversion of HNIW crystals to epsilon HNIW crystals is also disclosed.

26 Claims, 1 Drawing Sheet

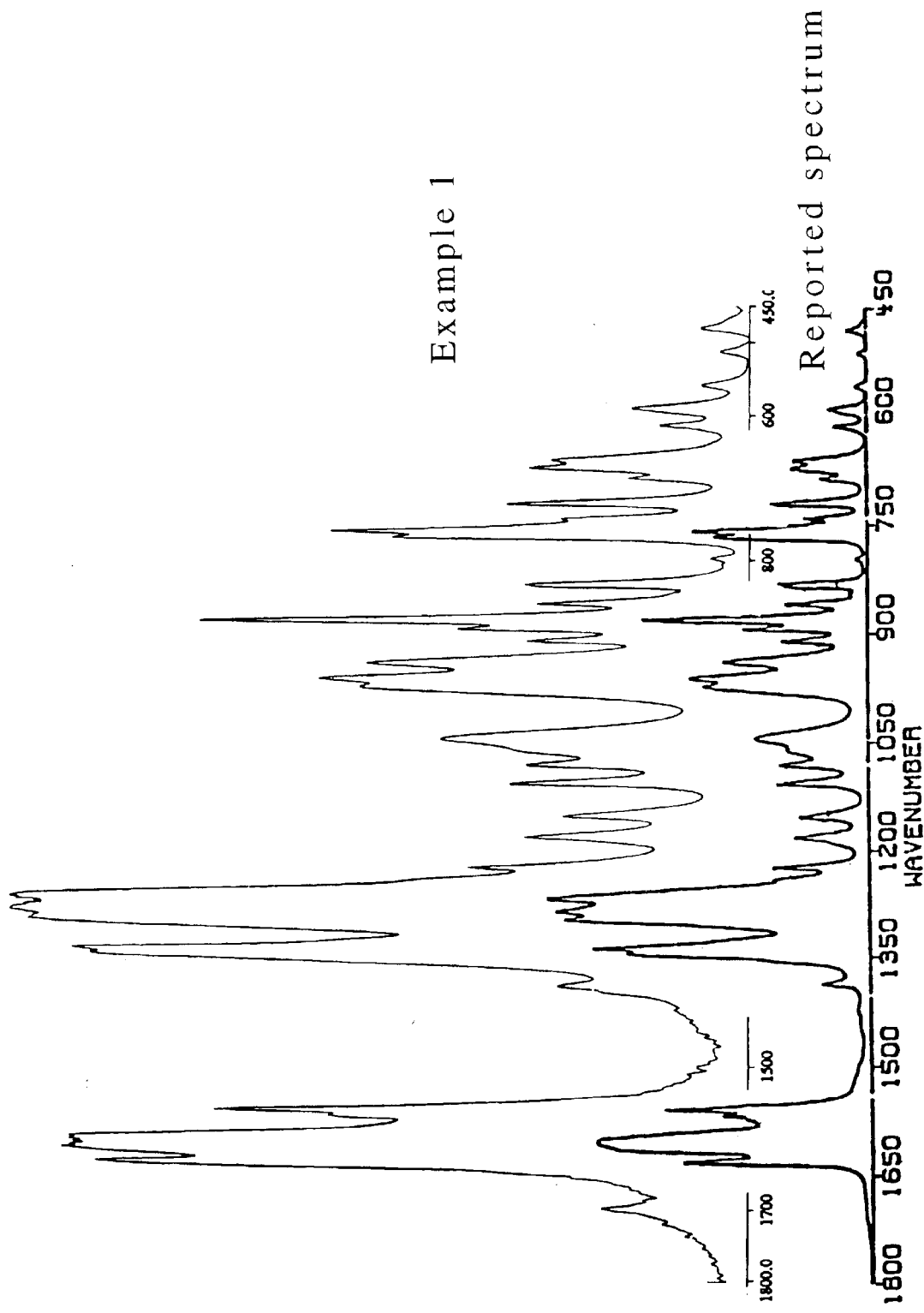

PROCESSES AND COMPOSITIONS FOR NITRATION OF N-SUBSTITUTED ISOWURTZITANE COMPOUNDS WITH CONCENTRATED NITRIC ACID AT ELEVATED TEMPERATURES TO FORM HNIW AND RECOVERY OF GAMMA HNIW WITH HIGH YIELDS AND PURITIES

RELATED APPLICATIONS

NONE

BACKGROUND OF THE INVENTION

The invention is directed to the field of energetic materials known as poly(N-nitro) dodecane cage compounds and processes to prepare these materials. In particular this invention relates to hexa(N-Nitro),hexaazatetracyclic dodecane compounds which are described in IUPAC nomenclature as 2,4,6,8,10,12-hexanitro-2,4,6,8,10,12-hexaazatetracyclo-[5.5.0.0$^{5,9}$.0$^{3,11}$]dodecanes. The parent compounds and corresponding skeleton structures have the common name of isowurtzitane. The skeletons are abbreviated as —HISW; the hexanitrohexaazaisowurtzitanes are abbreviated as HNIW; the compounds and the use of the nomenclature are described in U.S. Pat. No. 5,693,794.

The HNIW compounds have a density of about 2.0 g/cc and six N-nitro groups per molecule. The compounds are polymorphic with at least four crystal forms: alpha, beta, gamma and epsilon. Epsilon HNIW has the highest density. Typically the processes of production will result in the alpha HNIW which is then converted to the epsilon HNIW, see CA,Vol 128, NO.128, No.14, p.595, 167451w, Kawabe, et al, 1998. The product in the epsilon crystal form is preferred for use in energetic compositions such as propellants and explosives. The energetic compositions with HNIWs are described as Cl-20 containing compositions in U.S. Pat. Nos. 5,712,511, and 5,739,325. The preferred usage is to apply this term to the epsilon form of HNIW.

There are problems in developing compositions which utilize the epsilon HNIW as an energetic material. The intermediate HNIW crystal forms need to be available in high purity and yield. The processes for producing the intermediates need to be simplified. The reactions and reaction media need to reduce or eliminate the presence of side reactions, shock-sensitive impurities, other impurities and oxygenated -ISWs so that a high purity, shock insensitive epsilon HNIW crystal can be obtained. It is to these ends that this invention is directed.

BRIEF SUMMARY OF THE INVENTION

This invention provides nitration of N-substituted isowurtzitanes (NHISW) with a nitrating agent consisting essentially of concentrated nitric acid. The reaction is conducted at an elevated temperature and a solid product is recovered that is principally gamma HNIW. A novel process for converting the gamma HNIW to epsilon HNIW is also disclosed. Among the advantages of the invention are that the nitrating agent is highly concentrated nitric acid, a minimum molar excess of nitrating agent to HNIW can be used, the reaction temperatures can be increased and the yield of product is increased and the reaction reaches substantially total completion in a relatively short time.

The nitration processes of this invention directly produces a solid product that can be recovered as essentially pure gamma HNIW and the levels of impurities and side products in the product are reduced or eliminated. The conditions of the nitration can be controlled so that common impurities such as oxa-ISW and dioxa-ISWs and incompletely nitrolysed compounds such as PNAIW are present in only negligible amounts in the nitration media. Reaction promoters and solid proton donor resins can also be used in carrying out the practice of the invention. The optimum reaction conditions are such that yields of gamma HNIW are above about 99%. The invention allows the minimization of costs of production and the costs of waste disposal.

BRIEF DESCRIPTION OF THE FIGURE

The FIGURE contains representative FTIR spectrum of the gamma HNIW product of Example 1 and the reported spectrum from technical publications for gamma HNIW.

DETAILED DESCRIPTION OF THE INVENTION

In the practice of the invention, the principal reactants are the NHISW compounds and the concentrated nitric acid which are reacted at an elevated temperature for a relatively short time. The temperature needs to be at or above the onset temperature for the reaction to occur. As the reaction proceeds, an isolatable solid product will be formed. Significant amounts of HNIW crystals can be recovered from the product. They will be worked up so that a very pure form of gamma HNIW is obtained. This is converted to the epsilon HNIW.

The NHISW has N-substituents which are known as facile leaving groups; these can withstand the rigorous nitration conditions without destruction of the —ISW skeleton and allow the multiple nitrations at the N-sites which ultimately form the hexanitro compound. In effect the NO2 groups replace the facile leaving groups. While there are many potential facile leaving groups for the NHISWs, the problems of cost and availability are such that only a relatively few compounds are presently accessible. Generally, in terms of availability and efficacy, a preferred group of NHISWs are the compounds with skeletons whose N-substituents are selected from up to 6 hydrogen atoms, up to 6 alkyl groups, up to 6 acyl groups, up to 2 alkylaryl groups, up to 2 NO groups, and up to 2 NO2 groups. In terms of current availability, the particularly preferred substituents for the NHISW are hydrogen, acetyl, formyl, benzyl, NO,and NO2 groups. Exemplary compounds include tetraacetyldiformyl isowurtzitane (TADF), tetraacetyldibenzyl isowurtzitane (TADB), teraacetyldinitroso isowurtzitane and tetraacetyldinitro isowurtzitane (TADN).

The concentrated nitric acid reactant is historically considered to be HNO3 and H2O. The exact mechanism of the reactant is still poorly understood in complex nitration systems such as the present invention. The reactant will have an initial concentration of from about 90 to about 98% HNO3. As the reaction proceeds, the NO2 is consumed and the concentration of HNO3 becomes reduced. If the concentration falls to about 70%, the concurrent increase in the concentration of water is sufficient for attacks and decompositions of the HNISW at elevated temperatures. This leads to the oxa and dioxa ISWs and other impurities in the reaction media. In this invention, the reaction condition variables of elevated reaction temperature, choice of coreactant NHISW compounds, shortened reaction time and minimum molar excess of HNO3 can be selected to provide for high yields of gamma HNIW with minimum or undetectable impurities even though the concentration of water is increasing. The concentrated nitric acid is preferably at least about 90% HNO3 and may be from about 95 to about 98%

HNO3. Typically, the generally available 95% and 98% HNO3 grades are used.

Another advantage of this invention is that it employs simplified reaction procedures and advantageous ratios of reactants. The molar excess of HNO3 to NHISW is desirably is kept to a minimum. This appears to reduce impurities; it reduces the operating cost of the process and it reduces the waste disposal and clean up costs. The range of the molar excess can be from about 4 to about 6. This corresponds to about 24 to about 36 moles of HNO3 per mole of NHISW. It can also be appreciated that the minimum molar excess of nitrating agent is an advantage whether the reaction is conducted under either batch or continuous operations.

It is preferred to put the concentrated HNO3 in the reactor and then to add the NHISW compound in small portions and mix until a clear solution is formed. The mixing temperature should be in the range of about 20 to 25 degrees C. The temperature of the solution is gradually increased until a temperature is reached where the nitration of the NHISW will begin; this is considered the onset temperature and will be about 75 degrees C. for the conditions set forth in the Examples. It is the elevated temperature of the solution at which appreciable conversion to the HNISW occurs. In some cases, the onset temperature may be at about 80 degrees C. The upper limit for the elevated temperature will in theory be the boiling point of the reaction media. A lower temperature is practical. The Examples show that a temperature range of from about 100 to 115 degrees C. has given good results. A reaction temperature of about 115 degrees C. has been able to produce a gamma HNIW at very high yields and of very high purity with short reaction times. The exact temperature range will also be affected by the presence of solid reaction promoters and solid proton donor resins. These can increase recoverable gamma HNIW, lower onset temperature or decrease impurities.

The overall time of heating for the reaction to reach substantial completion varies within wide limits. The range is from about 3.5 to about 19 hours. It has been found that a short reaction time in the range of from about 3.5 to about 4 hours is adequate to achieve substantial completion of the reaction. Reaction times in the range of 12 and 12.5 to 19 hours have also been used which allow for a margin of safety in reaction control. Under batch reaction conditions, the system can reach about 100% completion.

The invention is also novel in the sense that it appears to be the first time that gamma HNIW is reported to be made by the use of concentrated nitric acid and elevated temperature. The presence of the gamma HNIW from the reaction is indicated by the formation of a white, solid material in the reaction medium that be worked up and identified as gamma HNIW from its FTIR spectrum. The work up and recovery of the HNIW follows the established practices in this field. When the reaction has reached the target degree of completion, the reaction medium will have a suspended solid in the reaction liquid. The system will be cooled to room temperature. Then, the materials will be poured over crushed ice. The solids will be recovered by filtration and examined with NMR. The solids represent the isolatable solid material of the reaction. The NMR will indicate the percentage of HNIW and the percentage of other materials. If oxa or dioxa ISWs are present, they can be identified as such. Further purification steps such as washing can be performed as discussed in Example 1. The high yield and high purity of the gamma HNIW of this invention is demonstrated by the FIGURE. The FTIR spectrum in the FIGURE for the product of the process is substantially as is shown by recognized technical literature publications for gamma HNIW.

The range of HNIW in the isolatable solid material from the reaction media is in the range of at least about 30% to about 99%. Intermediate contents of HNIW in the isolatable solids material were at least about 60%, 80% 95%, 97% and 98% are noteworthy. This HNIW is usually recovered and worked up by aqueous procedures By this stage, as well as in earlier stages, the HNIW can be principally in the gamma form. The gamma form can be converted to epsilon HNISW.

The practice of the invention is illustrated by the following Examples.

EXAMPLE 1

Part A

Preparation of Gamma HNIW by Nitration with 98% HNO3 at Elevated Temperature Part A of Example 1 illustrates the nitration reaction of the invention in which the reaction is carried out with 98% HNO3 as the nitrating agent, TADF as the NHISW and where the reaction temperature is about 115 degrees C. It demonstrates that the isolated, solid HNIW material that is converted to a gamma HNIW that has an FTIR spectra substantially the same as that reported for the pure gamma HNISW. Part B describes the conversion of the gamma HNIW to the epsilon HNIW. The yields and the purity of the gamma and epsilon HNIW are very high.

A three-necked, round-bottomed flask was fitted with a reflux condenser, a moisture-guard tube, a thermometer, and a stirrer. The equipment was placed in an oil bath. The nitrating agent was concentrated nitric acid in an amount of 15 ml at 98% HNO3 which was placed in the flask. The TADF was added in small portions at such a rate that the temperature of the reaction stays between about 20 and 25 degrees C. The media was stirred while the TADF went into solution. A total of 5.0 gm was added and the solution was clear.

After the addition was completed, the temperature of the reaction mixture was gradually elevated by heating the flask until a reaction temperature of about 115 degrees C. was reached. This temperature corresponds to an external oil bath temperature of 125 degrees C. As the reaction continued, a white, solid material began to form. As the reaction was allowed to continue, additional white solid material was formed. The total heating time was 4.5 hours.

When the reaction approached 100% conversion, the reaction mixture was cooled to room temperature and poured over crushed ice. The white, solid material was recovered by filtration and washing three times with cold water. It was air dried and formed a free-flowing powder. An FTIR spectrum of the product was taken and is shown in the FIGURE. There is a comparison with the published FTIR spectrum for pure gamma HNIW. It can be seen that the product produced by this invention is gamma HNIW of very high purity. The yield of gamma HNIW based on the amount of TADF was consistently in the range of from above about 90% to about 99%.

Part B

Polymorphic Transformation of

Gamma HNIW to Epsilon HNIW

This is a novel process to convert either alpha, beta or gamma HNIW to epsilon HNIW. Mixtures of the crystal forms may also be used. A 1.0 g. sample of gamma HNIW prepared as described above was mixed with 1 ml. Of acetic acid and 4.0 ml of ethyl acetate; this formed a solution. 0.030 gm of seed crystals of epsilon HNIW were added to the solution. Then, 24 ml of hexane were added dropwise to the mixture. A solid material precipitated. The mixture of liquid and solids was stirred for about 30 minutes and filtered. The solid filtrate was washed with hexane and dried to yield epsilon HNIW in quantitative yield. The epsilon HNIW crystals were free-flowing, white solids. If the acetic acid is not present, epsilon crystals are not obtained even with extreme standing times. The acetic acid allows the crystallization media to produce fine quality, epsilon HNIW.

EXAMPLES 2–5

In the following Examples 2–5, variations of the nitration conditions and the concentrated nitric acid reactant of Example 1 were used to demonstrate the effects of time, temperature (reported as internal reaction temperature), reaction promoters and reactant ratios on product yield, product purity and production of side products, by-products, impurities, etc.

The general procedure follows Example 1. The specified amount and type of concentrated nitric acid is put into the flask. The NHISW is added in small portions at such a rate that the temperature of the reaction stays between about 20 and 25 degrees C. while stirring the solution. After the addition is completed, the temperature of the reaction mixture is gradually elevated by heating until the target temperature is attained. The reaction is continued for the desired period of time. The reaction medium is separated into liquids and solid. The isolated solid material is examined by NMR. The approximate % of HNIW can be estimated from the NMR as well as the approximate % of other products. If oxa or dioxa isowurtzitanes were to be present, this can be noted.

(a) 300 mg of TADF were used to form a solution in 1 ml of 98% HNO3. The elevated temperature was about 80 degrees C. and the total time of heating was 4 hrs. A white solid product from the reaction was isolated. It was found to contain about 30% of HNIW and about 70% other products.

(b) The same conditions as in 2(a) above were used except the elevated temperature was at about 115 degrees C. The isolated material was found to contain at least about 98% HNIW and there was less than about 2% other products.

(c) The same conditions as in 2(a) above were used except the amount of TADF was 1,000 mg and the amount of 98% HNO3 was 1.5 ml. The elevated temperature was about 115 degrees C. and the total time of heating was 4 hrs. The isolated material contained about 80% HNIW and about 20% side products. Oxa and dioxa isowurtzitane impurities were among the side products; this indicates decomposition of HNIWs by water.

(d) The same conditions as in 2(c) above were used except the amount of TADF was 1,000 mg and the amount of 98% HNO3 was 2.0 ml. The isolated material was about 80% HNIW and the side products were about 20%. Oxaisowurtzitane was present in the side products; this indicates the decomposition of HNIWs by water.

(e) The same conditions as in 2( c) above were used except the amount of 98% HNO3 was 3 ml. The isolated material was about 98% HNIW and the side products were below about 2%.

(f)The same conditions as in Example 2(e) were used except the amount of materials were tripled. The isolated material was about 98% HNIW and the side products were below about 2%. This shows that the reaction conditions can be scaled up in a predictable manner to produce suitable products.

EXAMPLE 3

95% HNO3 as Nitration Agent

This Example illustrates the use of 95% HNO3 as the concentrated nitric acid for the reactions of this invention. It also illustrates that the molar ratios of reactants can be varied to minimize the amount of excess concentrated nitric acid required to drive the polynitration reaction and that the reaction conditions can be scaled up.

(a) 300 mg of TADF were used to form a solution with 1 ml of 95% HNO3. The elevated temperature was about 115 degrees C. and the total time of heating was 4 hrs. The content of the isolated material was in the range of from above about 95% HNIW to about 97% HNIW and the corresponding range for side products was from about 3% to below about 5%.

(b) 1,000 mg of TADF were used to form a solution with 3 ml of 95% HNO3. The elevated temperature was about 115 degrees C. and the total time of heating was 4 hrs. The content of the isolated material was in the range of from above about 95% HNIW to about 97% HNIW and the corresponding range for side products was from about 3% to about 5%.

(c) The conditions of 3(b) were duplicated except the amounts of materials were tripled. The content of the isolated material was in the range of from above about 95% HNIW to about 97% HNIW and the corresponding range for side products was from about 3% to about 5%. This illustrates that the conditions of the reaction can be scaled up.

EXAMPLE 4

Nitration with Concentrated Nitric Acid and Optionally Solid Reaction Promotors This Example illustrates that the reaction temperature has a strong effect on the onset of nitration of the NHISWs with the concentrated nitric acid and that at suitable temperatures the nitration can be conducted either with or without solid reaction promoters, such as solid proton donor resins.

(a) 300 mg of TADF were used to form a solution with 3 ml of 98% HNO3. 1300 mg of a solid resin having sulfonic acid groups in the proton form, available as Nafion-H, were also added to the solution. The elevated temperature was about 70 degrees C. The range of heating times were from about 12 to about 15 hours. No identifiable amount of HNIW was seen in the isolated material. The side products were not identified. This illustrates that nitration did not occur at this reaction temperature even in the presence of the concentrated nitric acid and the reaction promotor.

(b) The same conditions as in 4(a) above were used except the elevated temperature was at about 75 degrees C. The isolated material was about 60% HNIW and the side products were less than about 40%. The higher temperature reached the onset of nitration to form the HNIW product. The successful production was very evident.

(c) The same conditions as in 4(a) above were used except the elevated temperature was at about 80 degrees C.

The isolated material was about 80% HNIW and the side products were less than about 20%. The higher temperature produced more product. The successful production of solid white product was very evident.

(d) The same conditions as in 4(a) above were used except the elevated temperature was at about 100 degrees C. The isolated material was at least about 95% HNIW and the, side products were less than about 5%. Again, the higher temperature produced even more product.

(e) The same conditions as in 4(a) above were used except the elevated temperature was at about 115 degrees C. The isolated material was at least about 99% HNIW and the presence of other products can be described as nil.

EXAMPLE 5

Nitration with Varying Amounts of Solid Reaction Promoters at Same Reaction Temperature This Example illustrates the combined benefits that can occur from the optimization of reaction conditions which use the preferred temperature, the type and amount of concentrated nitric acid and the presence of the reaction promotor.

(a) 300 mg of TADF were used to form a solution with 3 ml of 98% HNO3. No reaction promotor was used. The elevated temperature was about 115 degrees C. The range of heating times were from about 12 to 15 hours. The isolated solid material was at least about 98% HNIW and the other products were present in amounts of less than about 2%. This is substantially a repetition of Example 2(f).

(b) The same conditions as in 5(a) above were used except a solid reaction promotor in the form of solid sulfonic acid resin in the protonated form, Nafion-H, was also present. It was used in an amount of 25 mg. The isolated solid material was at least about 98% HNIW and the other products were present in amounts of less than about 2%.

(c) The same conditions as in 5(b) above were used except the amount of Nafion-H was 100 mg. The isolated material was at least about 99% HNIW and there were no identifiable amounts of other products.

(d) The same conditions as in 5(b) above were used except the amount of Nafion-H was 300 mg. The isolated solid material was at least about 99% HNIW and there were no identifiable amounts of other products.

The detailed description and Examples are provided to illustrate specific modes of carrying out the invention.

The invention is intended to cover such equivalent practices, materials and supplementary techniques as would be evident to those skilled in the field and that the scope of the claims should be interpreted to that end.

We claim:

1.) A process for the preparation of hexanitrohexaazaisowurtzitane (HNIW) through the nitration of N-substituted, hexazaisowurtzitane (NHISW) with concentrated nitric acid by the steps of: (a) forming a solution consisting essentially of an NHISW and the concentrated nitric acid, and (b) heating the solution and maintaining the solution at a temperature of at least about 75 degrees C. for a time sufficient to produce a solid product containing HNIW.

2.) The process of claim 1 where the reaction temperature is in the range of from about 75 degrees C. to about 115 degrees C.

3.) The process of claim 1 where the reaction temperature is in the range of from about 80 degrees C. to about 115 degrees C.

4.) The process of claim 1 where the reaction temperature is in the range of about 100 degrees C. to about 115 Degrees C.

5.) The process of claim 1 where the reaction temperature is about 115 Degrees C.

6.) The process of claim 1 where the concentrated nitric acid has an initial concentration of from about 90 to about 98% HNO3 and the reaction temperature is in the range of from about 75 degrees C. to about 115 degrees C.

7.) The process of claim 2 where the initial concentration is from about 95 to 98% HNO3.

8.) The process of claim 2 where the initial concentration is about 95% HNO3.

9.) The process of claim 2 where the initial concentration is about 98% HNO3.

10.) The process of claim 1 where the N-substituents of the NHISW are facile leaving groups.

11.) The process of claim 10 where the facile leaving groups are selected from up to 6 hydrogen atoms, up to 6 alkyl groups, up to 6 acyl groups, up to 2 alkylaryl groups and up to 2 NO2 groups.

12.) The process of claim 11 where the N-substituents are selected from hydrogen, acetyl, formyl, benzyl and NO2 groups.

13.) The process of claim 10 where the concentrated nitric acid has an initial concentration of from about 90 to about 98% HNO3 and the reaction temperature is in the range of about 100 to about 115 degrees C.

14.) The process of claim 13 where the NHISW is tetraacetyl,diformylisowurtzitane.

15.) The process of claim 1 where the solid material is predominately NHIW.

16.) The process of claim 1 where the isolatable solid material contains at least about 30% HNIW.

17.) The process of claim 1 where the isolatable solid material contains at least about 60% HNIW.

18.) The process of claim 1 where the isolatable solid material contains at least about 80% HNIW.

19.) The process of claim 1 where the isolatable solid material contains at least about 95% HNIW.

20.) The process of claim 1 where the isolatable solid material contains at least about 97% HNIW.

21.) The process of claim 1 where the isolatable solid material contains at least about 98% HNIW.

22.) The process of claim 1 where the isolatable solid material contains at least about 99% HNIW.

23.) The reaction media produced by the process of claim 1 having an isolatable solid material with a content of HNIW of at least about 30%.

24.) The process of claim 1 where the concentrated nitric acid has an initial concentration of from about 90 to about 98% HNO3, the reaction temperature is in the range of from about 75 degrees C. to about 115 degrees C. and the molar ratio of HNO3 to NHISW is in the range of about 24 to about 36.

25.) The process of claim 24 where the reaction temperature is in the range of from about 100 degrees C. to about 115 degrees C.

26.) The process of claim 22 where the substituents on the NHISW include four acetyl groups.

* * * * *